US012788903B2

(12) United States Patent
Mezhericher et al.

(10) Patent No.: US 12,788,903 B2
(45) Date of Patent: Nov. 10, 2026

(54) SYSTEM AND METHOD FOR AEROSOL PARTICLE PRODUCTION OF SUBMICRON AND NANO STRUCTURED MATERIALS

(71) Applicant: The Trustees of Princeton University, Princeton, NJ (US)

(72) Inventors: Maksym Mezhericher, Princeton, NJ (US); Howard A. Stone, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 894 days.

(21) Appl. No.: 17/917,598

(22) PCT Filed: Apr. 6, 2021

(86) PCT No.: PCT/US2021/025905
§ 371 (c)(1),
(2) Date: Oct. 7, 2022

(87) PCT Pub. No.: WO2021/207149
PCT Pub. Date: Oct. 14, 2021

(65) Prior Publication Data

US 2023/0143042 A1 May 11, 2023

Related U.S. Application Data

(60) Provisional application No. 63/006,188, filed on Apr. 7, 2020.

(51) Int. Cl.
*A61M 11/02* (2006.01)
*A61M 16/14* (2006.01)
(Continued)

(52) U.S. Cl.
CPC ............ *A61M 11/02* (2013.01); *A61M 16/14* (2013.01); *A61K 35/76* (2013.01); *A61K 36/3482* (2024.05);
(Continued)

(58) Field of Classification Search
None
See application file for complete search history.

(56) References Cited

U.S. PATENT DOCUMENTS 3,378,238 A 4/1968 Babington et al.
3,562,768 A 2/1971 Edquist et al.
(Continued)

FOREIGN PATENT DOCUMENTS

CS 208843 B1 10/1981
DE 4402758 A1 8/1995
(Continued)

OTHER PUBLICATIONS

Spray-freeze drying: A novel process for the drying of foods and bioproducts.*
(Continued)

*Primary Examiner* — Bradley H Philips
(74) *Attorney, Agent, or Firm* — Greenberg Traurig, LLP; George E. Banis

(57) ABSTRACT

Disclosed herein is a multi-purpose aerosol platform capable of producing and delivery of submicron and nano structured materials for pharmaceutical, biomedical and environmental applications. Depending on the application, active chemical and biological materials may be processed from liquid dispersions into droplets and/or particle formulations. The disclosed system uses moderate gas pressures to atomize liquids into submicron-size droplets that are 10-1000 times smaller in diameter than commercial and research systems. This allows much gentler and rapid droplet-to-particle con-
(Continued)

version, applying much smaller physical and chemical stresses on the processed materials than conventional techniques like spray drying, spray coating, spray freeze drying and other technologies. For example, the disclosed system can be used for an ultra-fine nebulization and delivery of viscous therapeutic oils including oils of medical cannabis, for which conventional nebulization systems either fail or became ineffective. Such systems could help patients with acute respiratory distress syndrome (ARDS) developed in hard COVID-19 cases.

8 Claims, 8 Drawing Sheets

(51) Int. Cl.

| | |
|---|---|
| *A61K 35/76* | (2015.01) |
| *A61K 36/185* | (2006.01) |
| *A61P 11/00* | (2006.01) |
| *B05B 7/00* | (2006.01) |
| *B05B 7/24* | (2006.01) |

(52) U.S. Cl.
CPC ............... *A61M 2202/0468* (2013.01); *A61M 2202/206* (2013.01); *A61M 2202/30* (2013.01); *A61P 11/00* (2018.01); *B05B 7/0012* (2013.01); *B05B 7/2489* (2013.01)

(56) References Cited

U.S. PATENT DOCUMENTS

| | | | | |
|---|---|---|---|---|
| 3,584,792 | A | 6/1971 | Johnson | |
| 3,595,443 | A | 7/1971 | Jones | |
| 3,814,322 | A | 6/1974 | Waldrum | |
| 4,233,891 | A | 11/1980 | Schindler et al. | |
| 4,322,378 | A | 3/1982 | Hendricks | |
| 4,743,407 | A | 5/1988 | Apel et al. | |
| 6,377,387 | B1 | 4/2002 | Duthaier et al. | |
| 6,464,886 | B2 | 10/2002 | Ganan-Calvo | |
| 8,261,726 | B2 | 9/2012 | Hassan et al. | |
| 10,384,218 | B2 | 8/2019 | Mezhericher et al. | |
| 2007/0119449 | A1 * | 5/2007 | Boehm | A61M 16/208 128/95.1 |
| 2008/0295831 | A1 | 12/2008 | Svehaug | |
| 2012/0085239 | A1 | 4/2012 | Sonoda et al. | |
| 2017/0312474 | A1 | 11/2017 | Forde | |

FOREIGN PATENT DOCUMENTS

| | | | | |
|---|---|---|---|---|
| EP | 3204169 | A1 | 9/2017 | |
| FR | 1499843 | A | 10/1967 | |
| GB | 775734 | A * | 5/1957 | B05B 7/0012 |
| WO | WO-9743048 | A1 * | 11/1997 | B05B 7/0475 |
| WO | 2016055993 | A1 | 4/2016 | |
| WO | 2019213112 | A1 | 11/2019 | |

OTHER PUBLICATIONS

Atomization of liquids by disintegrating thin liquid films using gas jets.*

Aerosol-assisted synthesis of submicron particles at room temperature using ultra-fine liquid atomization.*

Phage Therapy for Respiratory Infections Rachel Yoon Kyung Chang Adv Drug Deliv Rev. Aug. 2018 ; 133: 76-86. doi:10.1016/j.addr.2018.08.001.*

International Search Report & Written Opinion for corresponding PCT Application No. PCT/US2021/02905, dated Jul. 8, 2021.

International Search Report, and Written Opinion, for corresponding PCT Application No. PCT/IL2015/050857, dated Dec. 2, 2015.

Supplementary European Search Report for corresponding European Application No. 15848995.5, dated Apr. 19, 2018.

Stone, Howard A. and Mezhericher, Maksim, "Aerosol Production of Thermolabile Submicron and Nano-materials for Pharmaceutical and Biomedical Applications," Princeton University, Department of Mechanical and Aerospace Engineering, Apr. 2020.

Mezhericher, Maksim et al., "Aerosol-Assisted Synthesis of Submicron Particles at Room Temperature Using Ultra-Fine Liquid Atomization," Chemical Engineering Journal, vol. 346, pp. 606-620, 2018.

Mezhericher, Maksim et al., "Room-temperature Synthesis of Nanoparticles using New Aerosol-assisted Method".

Mezhericher, Maksim et al., supplementary material, "Room-temperature Synthesis of Nanoparticles using New Aerosol-assisted Method".

Mezhericher, Maksim and Stone, Howard A., "Room-temperature Synthesis of Nanoparticles and Nanostructures using a New Aerosol-assisted Technique," Princeton University, Department of Mechanical and Aerospace Engineering, Mar. 2017.

Mezhericher, Maksim et al., "Atomization of liquids by disintegrating thin liquid films using gas jets," International Journal of Multiphase Flow, vol. 88, pp. 99-115, Sep. 23, 2016.

Mezhericher, Maksim, "Atomization of Sodium Alginate-Water Solutions," Princeton University, Oct. 2016.

Mezhericher, Maksim, "Submicron aerosols of liquid fuels: Method of production, experimental characterization and a semi-empirical model," Applied Energy, vol. 235, pp. 1651-1663, 2019.

Supplementary European Search Report for corresponding EP Application No. 21784052, dated Feb. 2, 2024.

* cited by examiner

| Experimental Set | Atomizing System | Mean Droplet Diameter, µm | Code | Description of Liquid Sample | Calculated Coefficient of Bacteriophage Survival, ε |
|---|---|---|---|---|---|
| 1 | submicron droplet atomizer | 0.2 | 1/1 | taken before atomization from the atomizing chamber | 0.39 |
| | | | 1/2 | collected atomized droplets | |
| | | | 1/3 | taken after atomization from the atomizing chamber | |
| | | | 1/4 | repeat of the above experiment - taken before atomization from atomizing chamber | 0.41 |
| | | | 1/5 | repeat of the above experiment - collected atomized droplets | |
| | | | 1/6 | repeat of the above experiment - taken after atomization from atomizing chamber | |
| 2 | ultrasonic nebulizer | 5 | 2/1 | taken before atomization from the atomizing chamber | 0.24 |
| | | | 2/2 | collected atomized droplets | |
| | | | 2/3 | taken after atomization from the atomizing chamber | |
| | | | 2/4 | repeat of the above experiment - taken before atomization from atomizing chamber | 1.03 |
| | | | 2/5 | repeat of the above experiment - collected atomized droplets | |
| | | | 2/6 | repeat of the above experiment - taken after atomization from atomizing chamber | |
| 3 | pulverizer spray nozzle | 200 | 3/1 | taken before atomization from the atomizing chamber | 0.54 |
| | | | 3/2 | collected atomized droplets | |
| | | | 3/3 | taken after atomization from the atomizing chamber | |
| | | | 3/4 | repeat of the above experiment - taken before atomization from atomizing chamber | 0.71 |
| | | | 3/5 | repeat of the above experiment - collected atomized droplets | |

*FIG. 7*

SYSTEM AND METHOD FOR AEROSOL PARTICLE PRODUCTION OF SUBMICRON AND NANO STRUCTURED MATERIALS

CROSS-REFERENCE TO RELATED APPLICATIONS

This application claims priority to U.S. Provisional Patent Application No. 63/006,188, filed Apr. 7, 2020, which is hereby incorporated in its entirety by reference.

BACKGROUND

In recent years, there has been a world-wide increase in the rate of human disease involving antibiotic-resistant bacteria. According to the World Health Organization, antibiotic resistance today is one of the biggest threats to global health, food security, and development. The enhanced spread of such super bacteria requires finding alternative or supplementary ways to treat the corresponding infections. One prospective way is therapy using human-safe bacterial viruses known as bacteriophages, which have recently demonstrated their efficiency by helping to heal several patients thought to be in their terminal life stages due to infections caused by super bacteria *Acinetobacter baumannii, Mycobacterium abscessus, Pseudomonas aeruginosa* and others.

However, one of the major problems in manufacturing bacteriophage-containing preparations is the low survival rate of bacteriophages, due to their high sensitivity to many physical, chemical and bacterial factors, including temperature, humidity, pH, mechanical and thermal stresses, electrical and magnetic fields and presence of other viruses or microorganisms. For manufacturing effective bacteriophage-containing thermolabile pharmaceutical materials that could be widely used in medical, environmental, agricultural, aquacultural and other applications against bacterial infections, many open questions and technical problems should be addressed and resolved.

BRIEF SUMMARY

A first aspect of the present disclosure is a method for creating aerosols of droplets, aerosols of particles, or powders. The method generally comprises or consists of providing a liquid that includes a dispersed active chemical or biological material (such as a bacteriophage or an active pharmaceutical ingredient (API)), then aerating the liquid in an atomization chamber to form bubbles, such that the bubbles rise to a surface of the liquid. The liquid may optionally be, e.g., 5- 1000 times the viscosity of water. A submicron droplet aerosol is then formed by causing a gas jet to occur that is directed through an opening in a tube (generally, a hole through a wall of the tube) towards one of the bubbles. The pressure of the gas used to create the gas jet may be optionally based on the viscosity of the liquid.

Optionally, the method also includes forming a dry particle aerosol via solvent evaporation of the submicron droplet aerosol. The solvent evaporation may, for example, involve subjecting the droplet aerosol a gas having a temperature between 0° C. and 120° C., and/or may include lyophilization.

Optionally, the method also includes forming a powder of submicron or nano-structured particles by passing the dry particle aerosol through a particle collector.

In some embodiments, the submicron droplet aerosol or dry particle aerosol is provided to a patient. Optionally, such as when the patient is being treated with a ventilation machine, the submicron droplet aerosol or dry particle aerosol may be introduced in-line with the ventilation machine.

A second aspect of the present disclosure is a system for creating aerosols of droplets, aerosols of particles, or powders. The system includes a tube within an atomization chamber. The tube is configured such that it will be partially submerged in a liquid containing a dispersed active chemical or biological material. The tube contains openings through a side wall of the tube. At least some of the openings are arranged such that at a gas jet through the openings would be direct towards one or more bubbles on a surface of the liquid in the chamber, in order to form a submicron droplet aerosol.

The system may optionally also contain at least one chamber for solvent evaporation of the submicron droplet aerosol, and may optionally also contain a particle collector for collecting dry particles from the dry particle aerosol. The system may optionally be configured to provide the aerosols to a patient, such as via a mask.

BRIEF DESCRIPTION OF THE DRAWINGS

FIG. 7 is a table describing the examined liquid samples with T4 bacteriophages.

DETAILED DESCRIPTION

In many applications, active chemical and biological materials are processed from liquid dispersions into droplets and particle formulations. The disclosed system uses moderate gas pressures to atomize liquids into submicron-size droplets that are 10-1,000 times smaller in diameter than commercial and research systems. This allows much gentler and rapid droplet-to-particle conversion, applying much smaller physical and chemical stresses on the processed materials than conventional techniques like spray drying, spray coating, spray freeze drying and other technologies. These advantages enable better processing of delicate biomaterials, e.g., those sensitive to temperature, pH, humidity and other physicochemical parameters, for example bacteriophages that demonstrated as low as 1:1,000,000 survival rates (titer decrease) in conventional systems.

Additionally, the disclosed system is versatile and multipurpose. It can be used for: 1) nebulization of liquids and delivery of aerosols of submicron-size droplets; 2) production and delivery of aerosols of submicron/nano structured particles; 3) production of powders of submicron/nano structured particles. For example, the disclosed system can be used for an ultra-fine nebulization and delivery of viscous therapeutic oils including oils of medical cannabis, for which conventional nebulization systems either fail or became ineffective. Additional applications of the disclosed system are hospital nebulizers and inhalers capable of being directly coupled with ventilation machines. Such systems could help patients with acute respiratory distress syndrome (ARDS) developed in hard COVID-19 cases. The developed system has modular structure and can operate in both continuous and batch operation regimes. The disclosed system has no moving parts, it is simple and low-cost in manufacturing and maintenance, and no special materials are required for its construction. The production capacity of the disclosed system is scalable up and down, enabling production rates from order of 1 mg/h to order of 10 kg/h of droplet and particulate materials.

One aspect of the present disclosure is drawn to a method for creating aerosols of droplets, aerosols of particles, or powders. Some embodiments of the disclosed method may be best understood with reference to FIGS. 1-3.

Figure 1:
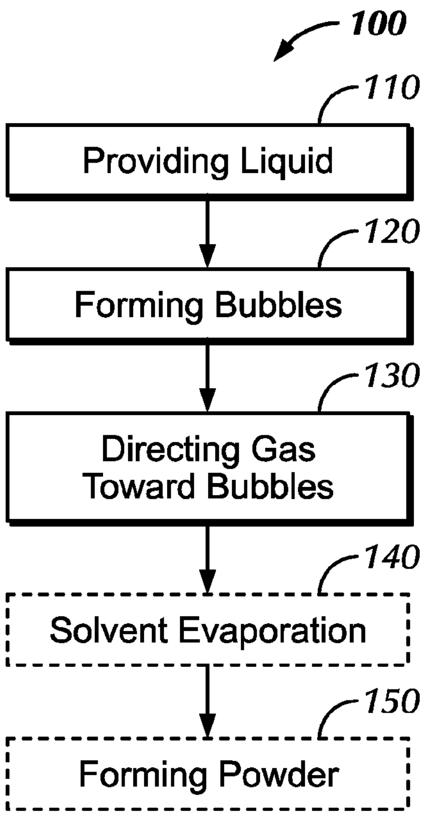
FIG. 1 is a flowchart of one embodiment of a method for aerosol particle production.

First referring to FIG. 1, the method (100) can be seen as generally requiring first providing (110) a liquid that comprises a dispersed active chemical or biological material.

The viscosity of the liquid is not particularly limited. In some embodiments, the viscosity is between 1 and 5 times that of water. In preferred embodiments, the viscosity of the liquid is between 5 and 1000 times that of water.

In some embodiments, the liquid consists, or consists essentially of, one or more solvents and one or more dispersed active chemical or biological materials. In some embodiments, the liquid consists, or consists essentially of, one solvent and one dispersed active chemical or biological material.

Active Chemical or Biological Material

The active chemical or biological material can be any appropriate material as understood by those of skill in the art, depending on the purpose of the aerosol.

The active chemical may include, for example, nutraceuticals, pharmaceuticals, and/or supplements.

For example, any drug, therapeutically acceptable drug salt, drug derivative, drug analog, drug homologue, or polymorph can be used in the present invention. Suitable drugs for use with the present invention can be found in the Physician's Desk Reference, $71^{st}$ Edition, the content of which is hereby incorporated by reference.

In certain embodiments, psychoactive drugs and analgesics, including but not limited to opioids, opiates, stimulants, tranquilizers, sedatives, anxiolytics, narcotics and drugs that can cause psychological and/or physical dependence can be used. In one embodiment, the drug for use in the present invention can include amphetamines, amphetamine-like compounds, benzodiazepines, and methyl phenidate or combinations thereof. In another embodiment, drugs may include any of the resolved isomers of the drugs described herein, and/or salts thereof.

Other non-limiting drugs that may be used include alfentanil, amphetamines, buprenorphine, butorphanol, carfentanil, codeine, dezocine, diacetylmorphine, dihydrocodeine, dihydromorphine, diphenoxylate, diprenorphine, etorphine, fentanyl, hydrocodone, hydromorphone, β-hydroxy-3-methylfentanyl, levo-α-acetylmethadol, levorphanol, lofentanil, meperidine, methadone, methylphenidate, morphine, nalbuphine, nalmefene, oxycodone, oxymorphone, pentazocine, pethidine, propoxyphene, remifentanil, sufentanil, tilidine, and tramodol, salts, derivatives, analogs, homologues, polymorphs thereof, and mixtures of any of the foregoing.

Further non-limiting examples of chemicals that may be utilized include dextromethorphan (3-Methoxy-17-methy-9a,13a,14a-morphinan hydrobromide monohydrate), N-{1-[2-(4-ethyl-5-oxo-2-tetrazolin-1-yl)-ethyl]-4-methoxymethyl-4-piperidyl}propionanilide (alfentanil), 5,5-diallyl barbituric acid (allobarbital), allylprodine, alpha-prodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methyl phenethylamine (amphetamine), 2-(α-methylphenethyl-amino)-2-phenyl acetonitrile (amphetaminil), 5-ethyl-5-isopentyl barbituric acid (amobarbital), anileridine, apocodeine, 5,5-diethyl barbituric acid (barbital), benzylmorphine, bezitramide, 7-bromo-5-(2-pyridyl)-1H-1,4-benzodiazepin-2(3H)-one (bromazepam), 2-bromo-4-(2-chlorophenyl)-9-methyl-6H-thieno[3,2-f][1,2,4]-triazolo[4,3-a][1,4]diazepine (brotizolam), 17-cyclopropylmethyl-4,5α-epoxy-7α[(S)-1-hydroxy-1,2,2-trimethyl propyl]-6-methoxy-6,14-endo-ethanomorphinan-3-ol (buprenorphine), 5-butyl-5-ethyl barbituric acid (butobarbital), butorphanol, (7-chloro-1,3-dihydro-1-methyl-2-oxo-5-phenyl-2H-1,4-benzodiazepin-3-yl)-dimethyl carbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine-4 oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]-diazepin-2(3H)-one (clotiazepam), 10-chloro-11b-(2-chlorophenyl)-2,3,7,11b-tetrahydrooxazolo[3,2-d][1,4]benzodiazepin-6(5H)-one (cloxazolam), (−)-methyl-[3β-benzoyloxy-2β(1αH,5αH)-tropane carboxylate (cocaine), 4,5α-epoxy-3-methoxy-17-methyl-7-morphinen-6α-ol (codeine), 5-(1-cyclohexenyl)-5-ethyl barbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl) propionate (dextropropoxyphene), dezocine, diampromide, diamorphone, 7-chloro-1-methyl-5-phenyl-1H-1,4-benzodiazepin-2(3H)-one (diazepam), 4,5α-epoxy-3-methoxy-17-methyl-6α-morphinanol (dihydrocodeine), 4,5α-epoxy-17-methyl-3,6α-morphinandiol(dihydromorphine), dimenoxadol, dimethyl thiambutene, dioxaphetyl butyrate, dipipanone, (6aR,10aR)-6,6,9-trimethyl-3-pentyl-6a,7,8,10a-tetrahydro-6H-benzo[c]chromen-1-ol (dronabinol), eptazocine, 8-chloro-6-phenyl-4H-[1,2,4]triazolo[4,3-a][1,4]benzodiazepine (estazolam), ethoheptazine, ethyl methyl thiambutene, ethyl-[7-chloro-5-(2-fluorophenyl)-2,3-dihydro-2-oxo-1H-1,4-benzodiazepin-3-carboxylate] (ethyl loflazepate), 4,5α-epoxy-3-ethoxy-17-methyl-7-morphinen-6a-ol (ethylmorphine), etonitrazene, 4,5α-epoxy-7a-(1-hydroxy-1-methylbutyl)-6-methoxy-17-methyl-6,14-endo-etheno-morphinan-3-ol (etorphine), N-ethyl-3-phenyl-8,9,10-trinorboman-2-ylamine (fencamfamine), 7-[2-(α-methylphenethylamino)-ethyl]theophylline (fenethylline), 3-(α-methylphenethylamino) propionitrile (fenproporex), N-(1-phenethyl-4-piperidyl) propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2-(3H)-one (flunitrazepam), 7-chloro-1-(2-diethyl aminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolo[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinan, 11-chloro-8,12b-dihydro-2,8-dimethyl-12b-phenyl-4H[1,3]oxazino[3,2-d][1,4] benzodiazepin-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenylheptan-3-yl acetate (levacetylmethadol (LAAM)), (−) dimethylamino-4,4-diphenyl-3-heptanone (levomethadone), (−)-17-methyl-3-morphinanol (levorphanol), levophenacyl morphan, lofentanil, 6-(2-chlorophenyl)-2-(4-methyl piperazinylmethylene)-8-nitro-2H-imidazo[1,2a][1,4]benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenetylamine (mefenorex), meperidine, 2-methyl-2-propyl trimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl-[2-phenyl-2-(2-piperidyl)acetate] (methyl phenidate), 5-ethyl-1-methyl-5-phenyl barbituric acid (methyl phenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl) acetamide (modafinil), 4,5α-epoxy-17-methyl-7-morphinene-3,6α-diol (morphine), myrophine, (±)-trans-3-(1,1-dimethylheptyl)-7,8,10,10α-tetrahydro-1-hydroxy-6,6-dimethyl-6H-dibenzo[b,d]pyran-9(6αH)-one (nabilone), nalbuphen, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2-(3H)-one (nordazepam), norlevorphanol, 6-dimethylamino-4,4-diphenyl-3-hexanone (normethadone), normorphine, norpipanone, the coagulated juice of the plants belonging to the species *Papaver somniferum* (opium), 7-chloro-3-hydroxy-5-phenyl-1H-1,4-benzodiazepin-2-(3H)-one (oxazepam), (cis-trans)-10-chloro-2,3,7,11b-tetrahydro-2-methyl-11b-phenyloxazolo[3,2-d][1,4] benzodiazepin-6-(5H)-one (oxazolam), 4,5α-epoxy-14-hydroxy-3-methoxy-17-methyl-6-morphinanone (oxycodone), oxymorphone, plants and plant parts of the plants belonging to the species *Papaver somniferum* (including the subspecies *setigerum*) (*Papaver somniferum*), papaveretum, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl) barbituric acid (pentobarbital), ethyl-(1-methyl-4-phenyl-4-piperidine-carboxylate) (pethidine), phenadoxone, phenomorphan, phenazocine, phenoperidine, piminodine, pholcodeine, 3-methyl-2-phenyl morpholine (phenmetrazine), 5-ethyl-5-phenyl barbituric acid (phenobarbital), αα-dimethyl phenethyl amine (phentermine), 7-chloro-5-phenyl-1-(2-propinyl)-1H-1,4-benzodiazepin-2(3)-one (pinazepam), α-(2-piperidyl)benzhydryl alcohol (pipradol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl) propionamide, methyl-{3-[4-methoxycarbonyl-4-(N-phenylpropaneamido)piperidino]propanoate} (remifentanil), 5-sec.-butyl-5-ethyl barbituric acid (secbutabarbital), 5-allyl-5-(1-methylbutyl) barbituric acid (secobarbital), N-{4-methoxymethyl-1-[2-(2-thienypethyl]-4-piperidyl}propionanilide (sufentanil), 7-chloro-2-hydroxy-methyl-5-phenyl-1H-1,4-benzodiazepin-2-(3H)-one (temazepam), 7-chloro-5-(1-cyclohexenyl)-1-methyl-1H-1,4-benzodiazepin-2(3H)-one (tetrazepam), ethyl-(2-dim ethylamino-1-phenyl-3-cyclohexane-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinyl barbituric acid (vinylbital), (1R*,2R*)-3-(3-dimethylamino-1-ethyl-2-methyl-propyl) phenol, (1R,2R,4S)-2-[dimethylamino) methyl-4-(p-fluorobenzyloxy)-1-(m-methoxyphenyl) cyclohexanol, each optionally in the form of corresponding stereoisomeric compounds as well as corresponding derivatives, especially esters or ethers, and all being physiologically compatible compounds, especially salts and solvates.

In some embodiment, the method utilizes one or more opioids such as hydrocodone, hydromorphone, morphine and oxycodone and/or salts thereof.

Non-limiting examples of an API that may be utilized include inorganic synthetic drugs (such as Aluminum hydroxide, magnesium trisilicate, etc.), or organic synthetic drugs (such as aspirin, chloramphenicol, caffeine, etc.). APIs may also include antibiotics (such as Aminoglycosides such as Amikacin, Gentamicin, Kanamycin, etc.), Ansamycins (such as Geldanamycin, Herbimycin, etc.), Carbapenems (sch as Ertapenem, Doripenem, Cilastatin, etc.), Cephalosporins (including 1$^{st}$, 2$^{nd}$, 3$^{rd}$, 4$^{th}$, and/or 5$^{th}$ generation Cephalosporins such as Cefadroxil, Cefazolin, Caphradine, Cefaclor, Cefoxitin, Cefonicid, Cefixime, Cefdinir, Cefdotaxime, Cefepime, Ceftaroline fosamil, Ceftobiprole, etc.), Glycopeptides (such as Teicoplanin, Vancomycin, etc.), Licosamides (such as Clindamycin, etc.), Lipopetides (such as Daptomycin), Mecrolides (such as Azithromycin, Clarithromycin, Fidaxomicin, etc.), Monobactams (such as Aztreonam), Nitrofurans (such as Furazolidone), Oxazolidinones (such as Linezolid, etc.), Penicillins (such as Amoxicillin, etc.), Polypeptides (such as Bacitracin, Colistin, Polymyxin B, etc.), Quinolones/Fluoroquinolones (such as Ciprofloxacin, Enoxacin, Levofloxacin, etc.), Sulfonamides (such as Mafenide, Sulfacetamide, etc.), and Tetracyclines (such as Demeclocycline, Doxycycline, etc.). APIs may also include various phytochemicals or phytochemal containing compounds, including phytoestrogens such as genistein and daidzein, such as isoflavones (e.g., soy isoflavones), flavonoids, phytoalexins (e.g., resveratrol (3,5,4'-trihydroxystilbene)), red clover extract, and phytosterols.

Other active chemicals can include, e.g., essential fatty acids, including polyunsaturated fatty acids, such as omega-3 fatty acids, omega-6 fatty acids, omega-9 fatty acids, conjugated fatty acids, and other fatty acids; oil soluble vitamins, including vitamin D3 and vitamin A palmitate; alpha lipoic acid; other oils; coenzymes, including Coenzyme Q10; and carotenoids, including lycopene, lutein, and zeaxanthin.

Other active chemicals can include therapeutic compounds in various therapeutic oils or plant extracts, including but not limited to cannabinoids, such as cannabidiol. In some embodiments, cannabis oil is utilized.

Other active chemicals can include inorganic materials, including graphene or graphene oxide, and metal oxides such as aluminum oxide, calcium oxide, chromium oxide, cobalt oxide, iron oxide, lead oxide, lithium oxide, silicon dioxide, titanium dioxide, and/or zinc oxide.

Other active chemicals can include industrially useful organic materials, including alkanes and unsaturated hydrocarbons.

Other active chemicals can include foods or food additives, including, e.g., NaCl.

In addition to active chemicals, any appropriate biological material may be utilized as well. For example, in some embodiments, the biological material is a biomolecule. That is, a compound comprising of one or more chemical moieties typically synthesized in living organisms. Non-limiting examples of biomolecules include amino acids, nucleotides, polysaccharides or simple sugars, lipids, or a combination thereof.

In some embodiments, the biological material comprises a cell and/or cell debris, in contrast to a purified biomolecule (e.g., a purified enzyme). In some embodiments, the biological material may be, or may be obtained from, viruses (e.g., bacteriophages), cells (e.g., microorganisms), tissues, and organisms (e.g., plants) using conventional, known techniques.

Solvent

The liquid will generally contain at least one solvent. A preferred embodiment utilizes water as a solvent, but other solvents may be included. In some embodiments, the solvent is a pharmaceutically acceptable solvent. Non-limiting examples of pharmaceutically acceptable solvents include ketones such as acetone, alcohols such as methanol, ethanol, or propanol, a mixture thereof, and a mixed solvent of water with one or more of these solvents. These pharmaceutically acceptable solvents may be used alone or as an appropriate combination of two or more thereof.

In some embodiments, the liquid is non-aqueous. In some embodiments, the solvent is an oil fit for human consumption, such as castor oil, soybean oil, sunflower oil, coconut oil, hemp oil or olive oil. In some embodiments, the solvent comprises, consists essentially of, or consists of one or more saturated fatty acids, one or more unsaturated fatty acids, or a combination thereof.

The concentration of the active chemical or biological material that is present in the liquid is not particularly limited. Preferably, the active chemical or biological material can be dispersed in the liquid. In some embodiments, the concentration of the active chemical or biological material is between 0.01% and 99% by weight of the liquid. In some embodiments, the concentration of the active chemical or biological material is between 0.01% and 50% by weight of the liquid. In some embodiments, the concentration of the active chemical or biological material is between 0.1% and 30% by weight of the liquid. In some embodiments, the concentration of the active chemical or biological material is between 1% and 20% by weight of the liquid.

Figure 2A:
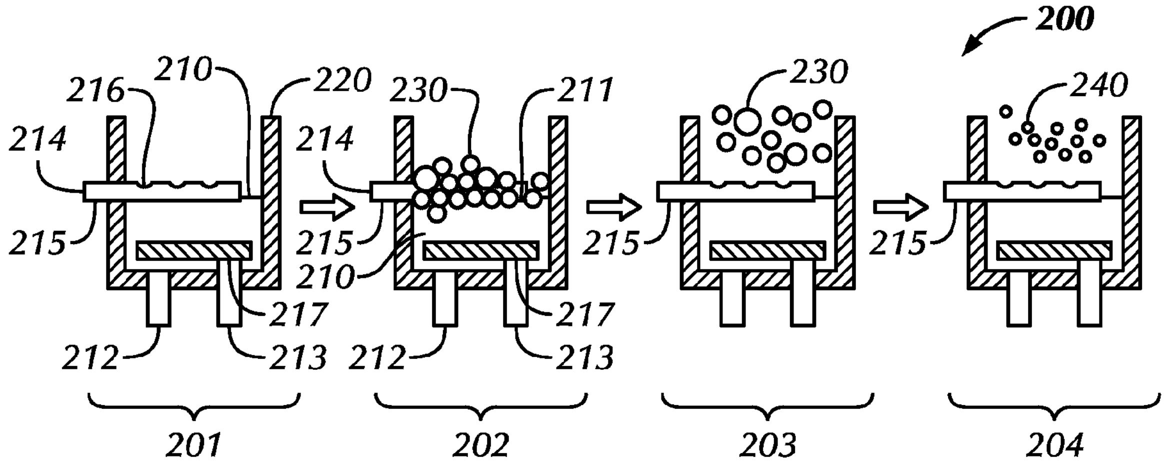
FIG. 2A is a graphical illustration of one embodiment of a method for aerosol particle production.

Referring to FIG. 2A, this first step described above is shown in the first stage (201) of FIG. 2A. In FIG. 2A, the disclosed method (200) is shown as generally involving providing the liquid (210) into a vessel (220). In preferred embodiments, the vessel is, or forms a portion of, an atomization chamber. The vessel is preferably comprised of glass, stainless steel, and/or any non-reactive material appropriate for containing the specific liquid in use. The vessel will generally be at least partially enclosed. The vessel (220) may have one or more inlets or ports (212, 213, 214). One inlet (212) may be configured to allow the liquid to be pumped into the vessel. As will be understood by those of skill in the art, the vessel may contain a sensor (not shown) configured to detect the level of the liquid in the vessel, and a processor (not shown) may be utilized to pump liquid into the vessel if the sensor determines a threshold level of liquid is not present. One inlet (213) may be configured to allow air to be pumped into the vessel to generate bubbles. As will be understood by those of skill in the art, this inlet may be operably connected to, e.g., a compressed gas storage tank (not shown) via at least one valve or regulator (not shown). And one inlet (214) may be configured to connect to a perforated tube or pipe (215), the perforated tube or pipe (215) configured to have a plurality of holes (216) through the tube or pipe wall, in order to allow a gas to be directed towards bubbles at or near the surface of the liquid. Preferably, the perforated tube or pipe (215) is positioned so as to be partially submerged, having at least some holes (216) above the surface of the liquid and at least some holes at or below the surface of the liquid. In some embodiments, the tube extends across the atomization chamber. In some embodiments, the tube is configured to allow more than one pressurized gas to be connected to it, thereby allowing a mixture of gasses to enter the atomization chamber through the tube. In some embodiments, the inlet (213) is operably connected to a one-way valve that is configured to allow a connection to the gas supply to be removably attached (e.g., via quick-disconnect fittings). In some embodiments, each end of the tube is operably connected to a one-way valve, and each one-way valve is configured to be removably connected to one or more gas supplies (e.g., one or more compressed gas tanks, etc.)

Figure 3:
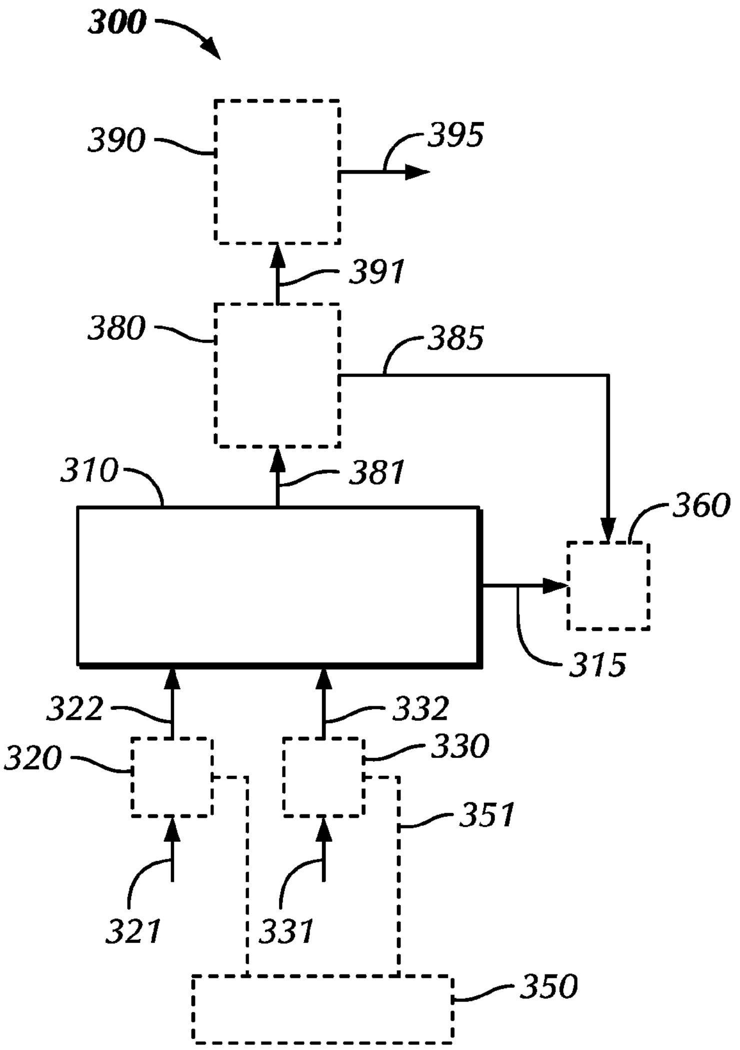
FIG. 3 is a schematic diagram of one embodiment of a system for aerosol particle production.

Referring to FIG. 3, this is also seen in some system (300) configurations, where an atomization chamber (310). In some embodiments, the atomization chamber is simply a volume of space that can contain the liquid while also having at least some vapor headspace above the level of the liquid. The liquid may optionally be introduced into the atomization chamber via an opening or inlet (322). In some embodiments, an optional pump (320) is used, which is connected (321) to a storage container containing the liquid. In some embodiments, the pump is a positive displacement pump. In some embodiments, the pump is a syringe pump. In some embodiments, the pump is operably connected to at least one processor (350) that controls at least some of the operation of the pump (320). The atomization chamber will preferably only have a single outlet through which submicron atomized droplets can leave the atomization chamber, and preferably, the droplets exit through a port or opening defined by a top portion of the atomization chamber. In some embodiments, each outlet is connected to a tube or channel, allowing the submicron atomized droplets to be directed away from the atomization chamber.

Referring back to FIG. 1, the method (100) continues by aerating the liquid in order to form (120) bubbles on and/or partially above the liquid surface. This can be done by any method known by those of skill in the art. For example, referring to FIG. 2A, a vessel may contain an aeration diffuser disc or ring (217) located near the bottom of the vessel, which is operably connected to an air inlet (213). As seem in the second stage (202), when air is provided to the aeration diffuser disc or ring (217), a multitude of bubbles are formed, which move towards the surface (211) of the liquid (210).

Figure 2B:
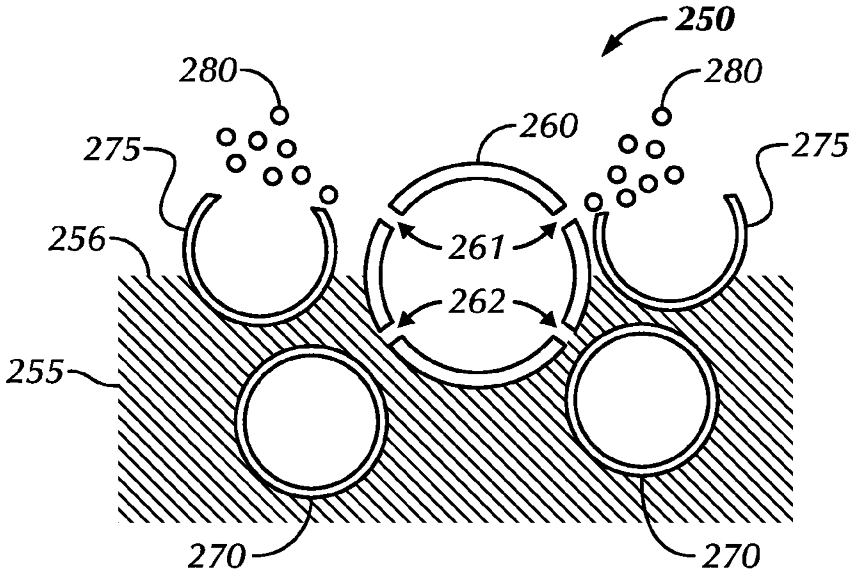
FIG. 2B is a graphical illustration of an embodiment of a perforated tube or pipe within an atomization chamber.

In a preferred embodiments, no aeration diffuser disc or ring (217) is utilized. Instead, an arrangement as depicted in FIG. 2B is utilized. In the preferred embodiment (250), a tube (260), and more preferably a flexible tube, with openings (e.g., ports, nozzles, perforations or holes) (261, 262) through the side walls of the tube is provided. The tube (260) is positioned within an atomization chamber such that at least some of the openings (261) are positioned above the air-liquid interface (sometimes referred to as just "the surface") (256) of the liquid (255), and at least some of the openings (262) are positioned below the surface (256). When a gas is provided to an inlet of the tube (260), bubbles (270) are first formed in the bulk liquid from gas exiting the openings (262) below the surface.

As seen in FIG. 3, an optional pressure regulator (330) is operably connected (through an inlet or opening (332)) to a aeration diffuser disc or ring, or other means for generating bubbles within the atomization chamber (310). The pressure regulator is connected (331) to a source of a gas. The gas may be air, $O_2$, $CO_2$, $N_2$, Ar, He, or any other gas as determined appropriate by a skilled artisan. The pressure regulator (330) may be connected to one or more processors (350), to allow the processors to control the pressure of the gas used to aerate the liquid.

Referring back to FIG. 1, the method (100) continues by causing a gas jet to be directed (130) towards at least one of the bubbles in an atomization chamber, forming a submicron droplet aerosol. Referring to FIG. 2A, this third step is visualized in stages two through four (202, 203, 204). There, by providing a gas through a gas inlet (214) through the perforated tube or pipe (215) positioned at or near the surface of the liquid, which had been generally surrounded by bubbles (230) (see the result of the second stage (202)), the bubbles (230) may optionally separate from the surface of the liquid (see third stage (203)) and into the air. At some point, the bubbles (230) will spontaneously disintegrate into submicron droplets (240). The disintegration may occur immediately upon the gas being directed at the bubbles, or it may occur within a short period of time afterwards, depending on a number of factors, including, e.g., the composition of the bubbles and the pressure of the gas directed at the bubbles.

In the preferred embodiment illustrated in FIG. 2B, as the bubbles (270) rise through the liquid and eventually rise at least partially above the surface (256) of the liquid (255), the bubbles will eventually have a gas jet directed at them from one of the openings (e.g., ports, nozzles, holes or perforations) (261) positioned above the surface of the liquid. That is, the openings (261) are configured such that when gas is provided to the tube, it causes a gas jet to be directed through an opening in a tube towards at least a portion of one of the bubbles in the atomization chamber. At that time, the bubbles will experience or exhibit a collapsing film (275), which eventually resulting in the formation of the aerosol of submicron droplets (280) that will be directed up and/or away from the surface of the liquid.

In some embodiments, the gas used in this step may be from the same source, or from a different source, as that used to aerate the liquid. As seen in FIG. 3, in some embodiments, the pressure regulator (330) that provides the gas used in this step may be connected to one or more processors (350), to allow the processors to control the pressure of the gas.

In some embodiments, the pressure fed to the atomization chamber for creating the gas jets may be based on the viscosity of the liquid, with less pressure required for less viscous liquids, and more pressure required for more viscous liquids. Typical pressures will range from 2 psig to 1000 psig, such as between 5 psig and 100 psig.

The flow rate of droplets produced by the disclosed bubble-gas jet atomizer can be adjusted easily, because the geometrical parameters of the atomizing tube and enclosing chamber along with the size of the ports, nozzles, holes, or perforations in the tube govern the droplet generation rate.

At this stage in the method, an aerosol of submicron droplets has been formed. In some embodiments, this is sufficient. As seen in FIG. 3, in some embodiments, the submicron droplet aerosol exits the atomization chamber (310) through a port or outlet (315). In some embodiments, some or all of the submicron droplet aerosol is transported to a collection device. In some embodiments, some or all the submicron droplet aerosol may be provided to a patient. For example, in FIG. 3, a mask (360) is operably connected (e.g., via tubes, valves, etc.) to the atomization chamber (310), the system being configured to allow the submicron droplet aerosol to be administered to the patient (e.g., via inhalation). In some embodiments, the atomization chamber is operably connected to a device that combines the submicron droplet aerosol with another material or treatment approach. For example, when a patient is being treated with a ventilation machine, the submicron droplet aerosol may be introduced in-line with the ventilation machine.

As shown in FIG. 1, the method (100) may comprise, consist essentially of, or consist of the previously described three steps (110, 120, 130). However, in some embodiments, some or all of the submicron droplet aerosol is further processed after leaving the atomization chamber. In particular, as shown in FIG. 1, a dry particle aerosol can be formed via solvent evaporation (140) of the submicron droplet aerosol. Any known technique for solvent evaporation can be utilized. For example, in some embodiments, some or all of the submicron droplet aerosol is exposed to a gas having a temperature between 0° C. and 120° C. In some embodiments, the solvent evaporation is via lyophilization. For example, as shown in FIG. 3, as the submicron aerosol droplets are transported away from the atomization chamber, through an outlet (381), they can be passed to a chamber (or series of chambers) (380) that first freeze the droplets, then dry the droplets via, e.g., sublimation and adsorption. Such techniques are well understood in the art.

At this stage in the method, an aerosol of dry particles has been formed. The dry particles may be submicron and/or nano structured material. In some embodiments, this will be sufficient. As seen in FIG. 3, in some embodiments, the dry particle aerosol may leave a chamber (380) used for solvent evaporation through a port or outlet (385). Similar to what may occur after the atomization chamber (310), in some embodiments, some or all of the dry particle aerosol may then be provided to a patient. For example, in FIG. 3, a mask (360) is operably connected (e.g., via tubes, valves, etc.) to the solvent evaporation chamber or chambers (380), the system being configured to allow the dry particle aerosol to be administered to the patient (e.g., via inhalation). In some embodiments, the atomization chamber is operably connected to a device that combines the dry particle aerosol with another material or treatment approach. For example, when a patient is being treated with a ventilation machine, the dry particle aerosol may be introduced in-line with the ventilation machine.

As shown in FIG. 1, the method (100) may comprise, consist essentially of, or consist of the previously described four steps (110, 120, 130, 140). However, in some embodiments, the method (100) may also include the fifth step of forming (150) a powder by passing some or all of the dry particle aerosol through a particle collector. This is seen in FIG. 3, where the solvent evaporation chamber(s) (380) feed into an inlet or opening (391) of a particle collector (390). In some embodiments, the dry powder is transported through an outlet or opening (395) to, e.g., a storage container (not shown), via a pump (not shown). The dry powder may be submicron and/or nano structured material.

It will be recognized that the disclosed system may have a modular structure, and is capable of operating in a continuous operation regime, a batch operation regime, or it can be converted between the two as needed. It will be understood that the primary limiting factor will be the ability to supply the liquid to the atomization chamber.

It will also be recognized that the disclosed system has no moving parts, it is simple and low-cost in manufacturing and maintenance, and no special materials are required for its construction, beyond those required to prevent the components from reacting with the liquid or atomization gas.

It will also be recognized that the production capacity of the disclosed system is scalable up and down, to meet almost any required 1 mg/h to 10 kg/h of droplet and/or particulate materials.

The disclosed liquid atomization process can be analyzed by applying the law of mass conservation and the First Law of Thermodynamics for a control volume around the atomization chamber, with liquid and atomizing gas entering, and droplets, vapor, and atomizing gas exiting. Assuming steady-state flow for a continuous adiabatic process at room temperature, neglecting the changes in potential energy of both fluids, evaporation and the change in liquid kinetic energy, assuming complete ideal expansion of the gas jet, and disregarding drag, one gets: $e_{\Delta p}=e_c+e_v$ [Eq. 1], where $e_{\Delta p}$, $e_c$, and $e_v$, where are respectively specific energies supplied by the gas pressure and stored or dissipated by the surface tension and viscosity of the atomized liquid.

Using dimensional analysis, it can be established that two dimensionless groups, $$La_d = \rho_l \gamma_l d / \mu_l^2$$

and $N_d=\Delta p_{gj} d/\gamma_l$, play the central role for determining droplet diameters. Here, $\rho_l$, $\gamma_l \mu_l$ are density, surface tension and dynamic viscosity of the liquid, $\Delta p_{gj}=p_g-p_\infty$ is the pressure drop across the nozzle producing the gas jet, and d is droplet diameter. Using the characteristic timescales of the liquid atomization, including the supplied energy of the gas jet $$\tau_{\Delta p} \sim \left(\rho_l l_c^2 / \Delta p_{gj}\right)^{1/2},$$

and capillary Rayleigh breakup $$\tau_c \sim \left(\rho_l l_c^3 / \gamma_l\right)^{1/2},$$

and viscous dissipation $$\tau_v \sim \rho_l l_c^2 / \mu_l$$

in the liquid, with the approximation for all the phenomena, the dimensionless groups can be expressed as timescale ratios $$La_d \sim \tau_v^2/\tau_c^2 \text{ and } N_d \sim \tau_c^2/\tau_{\Delta p}^2.$$

On the other hand, the energy scales and timescales are connected, $$e_{\Delta p} \sim l_c^2/\tau_{\Delta p}^2,\ e_c \sim l_c^2/\tau_c^2, \text{ and } e_v \sim l_c^2/\tau_v^2,$$

and one can again assume $l_c=d$. Therefore, $La_d \sim e_c/e_v$ and $N_d \sim e_{\Delta p}/e_c$, or $La_d=k_1 e_c/e_v$ and $N_d=k_2 e_{\Delta p}/e_c$, where $k_1$ and $k_2$ are proportionality coefficients. Substituting the two latter expressions into Eq. 1, one gets:

$$N_d = k_1 + k_1 k_2 La_d^{-1}. \quad \text{[Eq. 2]}$$

The obtained equation connects between the specific energies provided by the gas jets and dissipated by the atomized liquid in nondimensional form and determines the diameters of the produced droplets.

The balance of specific energy rates in the atomization can be obtained by taking the time derivative of Eq. (1): $\varepsilon_{\Delta p}=\varepsilon_c+\varepsilon_v$ [Eq. 3].

Employing the dimensionless analysis and algebraic manipulations similar to those performed above for droplet diameters, two dimensionless numbers $$N_{l,cv} = \rho_l^2 \gamma_l d^3 \dot{n}_d / \mu_l^3 \text{ and } N_{l,pc} = \Delta p_{gj}^{3/2} / \left(\gamma_l \rho_l^{1/2} \dot{n}_d\right)$$

playing the central role for droplet flow rates are established, where $\dot{n}_d$ is droplet production rate. Correspondingly, $N_{l,cv} \sim \varepsilon_c/\varepsilon_v = k_3 \varepsilon_c/\varepsilon_v$ and $N_{l,cv} \sim \varepsilon_{\Delta p}/\varepsilon_c = k_4 \varepsilon_{\Delta p}/\varepsilon_c$, where $k_3$ and $k_4$ are proportionality coefficients. Substituting into Eq. 3, one gets:

$$N_{l,pc} = k_3 + k_3 k_4 N_{l,cv}^{-1}. \quad \text{[Eq. 4]}$$

The obtained equation connects the rates of specific energies provided by the gas jets and dissipated by the atomized liquid in nondimensional form and determines the flow rates of the produced droplets.

Figure 4A:
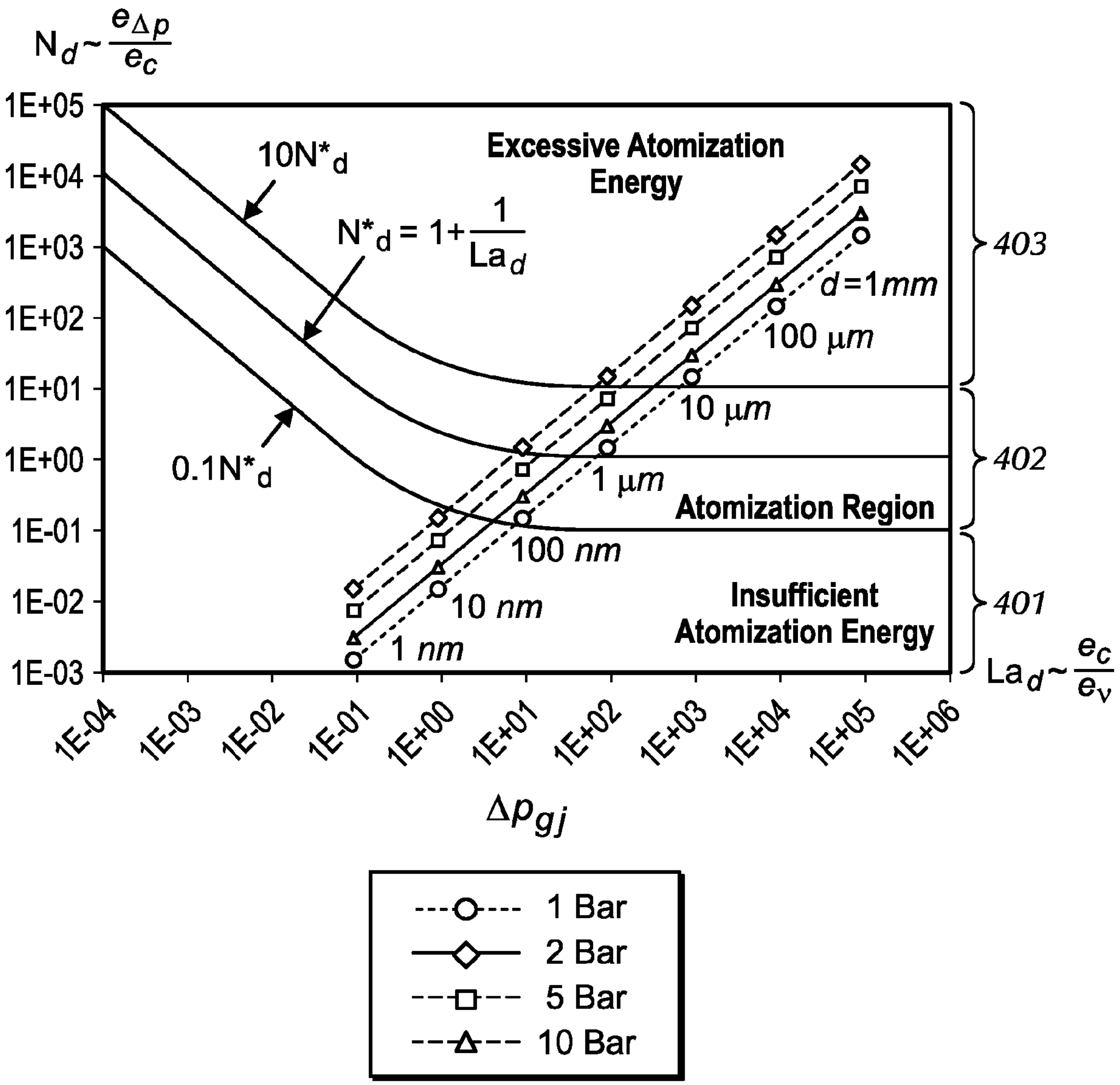
FIG. 4A is a graph showing exemplary atomization diagrams for diameters.
Figure 4B:
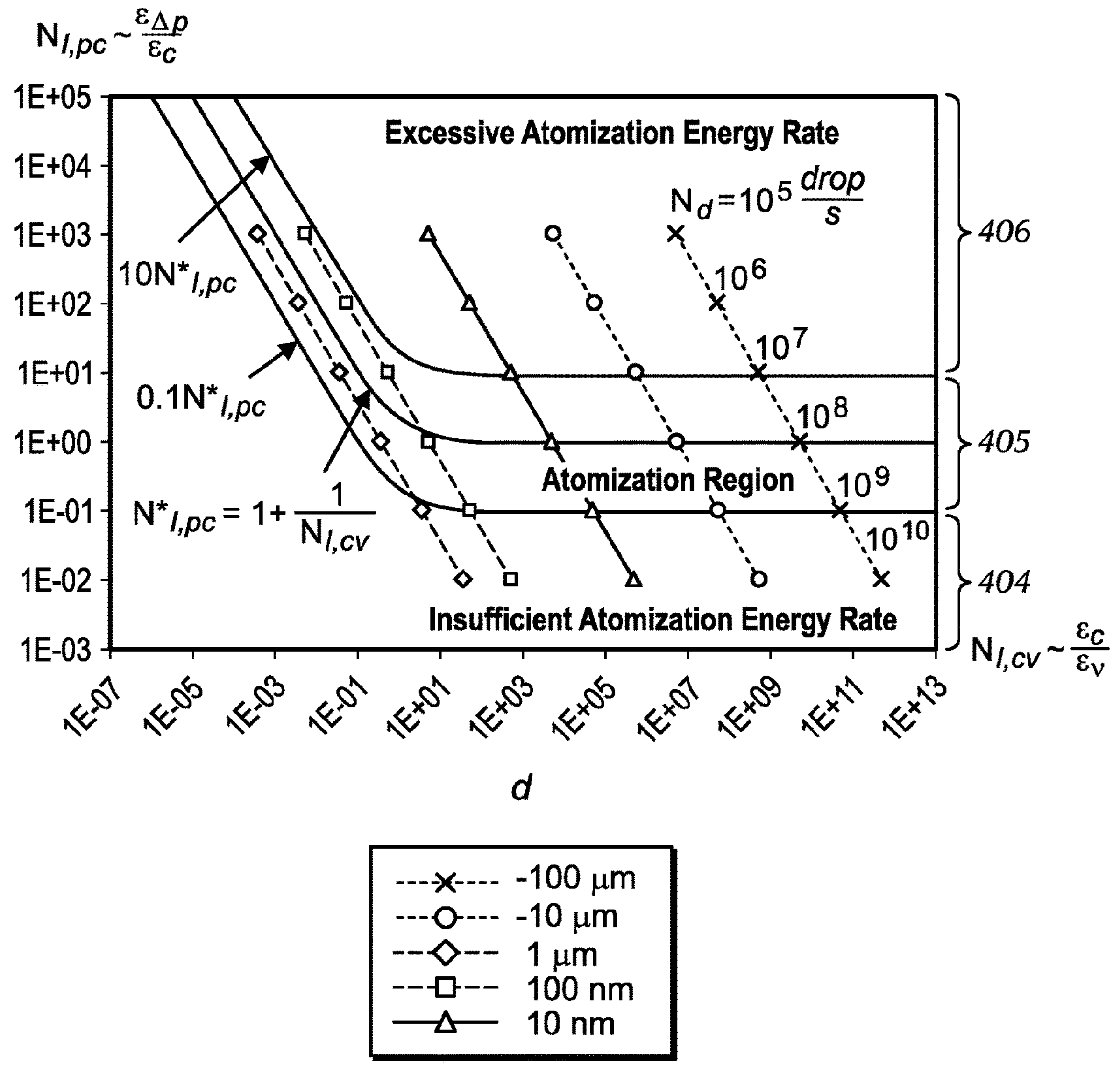
FIG. 4B is a graph showing exemplary atomization diagrams for flow rates of water droplets.

In the above discussion, the nomenclature used is as follows:

- $e_{\Delta p}$ is the specific energy supplied by the gas pressure; $e_c$ is the specific energy stored or dissipated by the surface tension of the liquid; $e_v$ is the specific energy stored or dissipated by the viscosity of the liquid;
- $\rho_l$ is the density of the liquid;
- $\gamma_l$ is the surface tension of the liquid;
- $\mu_l$ is the dynamic viscosity of the liquid;
- $\Delta p_{gj}$ is the pressure drop across the nozzle producing the gas jet; d is droplet diameter; $p_g$ is estimated as the pressure of the supply gas used to create the gas jet; $p_\infty$ is estimated as the ambient pressure in the atomization chamber;
- $\dot{n}_d$ is the droplet production rate;
- $\varepsilon_{\Delta p}$ is the specific energy rate supplied by the gas pressure; $\varepsilon_c$ is the specific energy rate stored or dissipated by the surface tension of the liquid; $\varepsilon_v$ is the specific energy rate stored or dissipated by the viscosity of the liquid;
- $k_1$, $k_2$, $k_3$, and $k_4$ are proportionality coefficients;
- $La_d$ is a Laplace number for the droplet, representing the ratio of energies dissipated by surface tension and viscosity;

$\tau_{\Delta p}$ is the characteristic timescale of the supplied energy of the gas jet; $\tau_c$ is the characteristic timescale of the capillary Rayleigh breakup; $\tau_v$ is the characteristic timescale of the viscous dissipation in the liquid;

$N_{l,cv}$ is a dimensionless number representing ratio of energy rates dissipated by liquid surface tension and viscosity $N_{l,pc}$ is a dimensionless number representing ratio of energy rates supplied by gas and dissipated by liquid surface tension Examples of this can be seen in the atomization diagrams for diameters and flow rates of water droplets shown in FIGS. 4A and 4B. The droplet diameter and gas jet pressure were varied in FIG. 4A, and the droplet production rate and droplet diameter were varied at $\Delta p_{gj}$=2.5 bar in FIG. 4B. The central lines of atomization region on those diagrams were obtained from Eqs. (2) and (4), assuming the proportionality coefficients to be order of unity. The lower and upper boundaries of the atomization region are calculated by assuming tenfold difference of the dimensionless numbers $N_d$ (FIG. 4A) and $N_{l,pc}$ (FIG. 4B) with respect to those of the corresponding central lines $$N_d^* = 1 + La_d^{-1} \text{ and } N_{l,pc}^* = 1 + N_{l,cv}^{-1}.$$

From FIG. 4A for $\Delta p_{gj}$=2.5 bar, one can calculate that the atomization process is expected to generate droplets with diameters in the range 40 nm-3 μm, and mean droplet diameter ~300 nm. In experimental studies, the arithmetic mean diameter was ~250 nm and the upper boundary of the obtained number based droplet size distribution was ~3 μm, whereas the lowest measured droplet diameter was set by the measuring range 100 nm-900 μm of the utilized laser scattering device.

For the calculated mean diameter of 300 nm, FIG. 4B yields $10^8$ drop/s, while $10^7$ drop/s were measured experimentally. This difference can be attributed to a theoretical assumption of a continuous atomization process, while in fact there is a periodic disintegration (by a gas jet) of bubbles rising to the liquid surface (see FIG. 2B). The calculations for all other liquids considered, which included gasoline, diesel, and solutions of sodium alginate, also demonstrated good agreement between the theory and experiment.

Finally, it is worth noting that for the region of $La_d \geq 1$ in FIG. 4A, the distribution of droplet diameters in the atomization region follows a log-normal law, which is widely observed in technical and natural liquid atomization processes.

A user should preferably design their systems to stay within the "atomization region" (402, 405) depicted in FIGS. 4A and 4B (that is, having $N_d$ or $N_{l,pc}$ value that are between 0.1 and 10 times the central $N^*_d$ or $N^*_{l,pc}$ value, respectively). In those diagrams, the central line of that region (given by the equations described above) provide the expected (i.e., mean) droplet diameters and production rate of droplets (i.e., number of droplets produced per unit time).

The droplet diameters which are in the region "insufficient atomization energy" (401, 404) (that is, having an $N_d$ or $N_{l,pc}$ value that is less than 1/10 of the central $N^*_d$ or $N^*_{l,pc}$ value, respectively) are too small, and unlikely to be produced by the process. In that operating range, there is not enough energy supplied into the process to overcome liquid surface tension and viscosity.

The droplet diameters which are in the region "excessive atomization energy" (403, 406) (that is, having an $N_d$ or $N_{l,pc}$ value that is more than 10 times the central $N^*_d$ or $N^*_{l,pc}$ value, respectively) are too big to likely be produced by the process. In that operating range, there is too much energy supplied into the process, much more than that needed to overcome liquid surface tension and viscosity. Such big droplets, if initially pinched off from the liquid, will be subsequently disintegrated into smaller droplets using the supplied energy excess over the liquid surface tension and viscosity. In addition, the excess of the energy supplied with the gas phase, can produce non-negligible changes in kinetic energies (e.g., turbulence) and enthalpies (e.g., adiabatic jet expansion with substantial temperature change by Joule-Thomson effect) of the interacting fluids that should be taken into account in such cases.

Example 1

To study the survival of bacteriophages during preparation of functional particulate formulations from phage-containing solutions, all the stages of the process were investigated. The formulation process includes the following stages: preparation of concentrated bacteriophage lysate, dilution of the lysate in a buffer solution, atomization of obtained bacteriophage solution into spray or aerosol droplets, evaporation of solvent from the atomized droplets and drying-induced transformation of droplets into particles, and collection of particulate products from carrying gas phase.

In this example, the survival of bacteriophages during atomization of bacteriophage solutions into spray or aerosol droplets was studied and compared five different liquid atomization technologies: jet nebulizer (Omron CompAIR NE-C801), ultrasonic nebulizer (Lumiscope Portable LMS-6700), vibrating mesh nebulizer (Omron MicroAir NE-U100), pulverizer spray nozzle (Mainstays Ironing Spray Bottle), and the disclosed submicron droplet atomizer. Each atomization technique differs by the employed physical phenomena and the resulting droplet size distribution. For water as a liquid to be atomized, jet, ultrasonic and vibrating mesh nebulizers generate droplets of 3-7 μm in mean diameter, whereas the disclosed submicron droplet atomizer produces much smaller droplets, ~200 nm in mean diameter and a pulverizer spray nozzle generates substantially bigger droplets of 100-700 μm in diameter.

The survival of two types of model bacteriophages was investigated: T4 and P1. Bacteriophage T4 is a virulent coliphage that infects *Escherichia coli* bacteria by undergoing a lytic lifecycle, which results in destruction of the infected bacterium cell and its membrane. Bacteriophage P1 is a temperate coliphage that infects *Escherichia coli* and some other bacteria by undergoing a lysogenic lifecycle, in which a circular replicon (plasmid) in the bacterial cytoplasm is formed and the host bacterium continues to live and reproduce normally, until at later events (such as UV radiation or the presence of certain chemicals) proliferation of new phages via the lytic cycle occurs.

The initial concentration of the phages in both lysates was $10^{10}$-$10^{11}$ pfu/mL, as measured by the suppliers. The unit "pfu/mL" (plaque forming units per milliliter) indicates the number of infective particles within one milliliter of the volume sample as measured by the known plaque assay techniques, and is based on the assumption that each formed plaque corresponds to one infective virus particle. Before the experiments, the initial lysates were diluted one hundred times using an in-house prepared TM buffer (also known as TRIS MgSO4 buffer solution, pH=7.4 at 25° C.). The utilized water was deionized by means of the laboratory EDM Millipore Mili-Q/Q-POD water purification system.

The buffer solution was autoclaved before the usage in Primus Sterilizer PSS5-A-MESD. The pH of the solution was measured using PHM220 MeterLab Radiometer Analytical pH meter.

To reliably and safely collect for further analysis the generated droplets out of the produced aerosols containing bacteriophage, an experimental setup including three levels of protection was developed. One of the five studied atomizing devices was filled with prepared bacteriophage solution that had known concentration of active bacterium-infecting phage particles.

Figure 5:
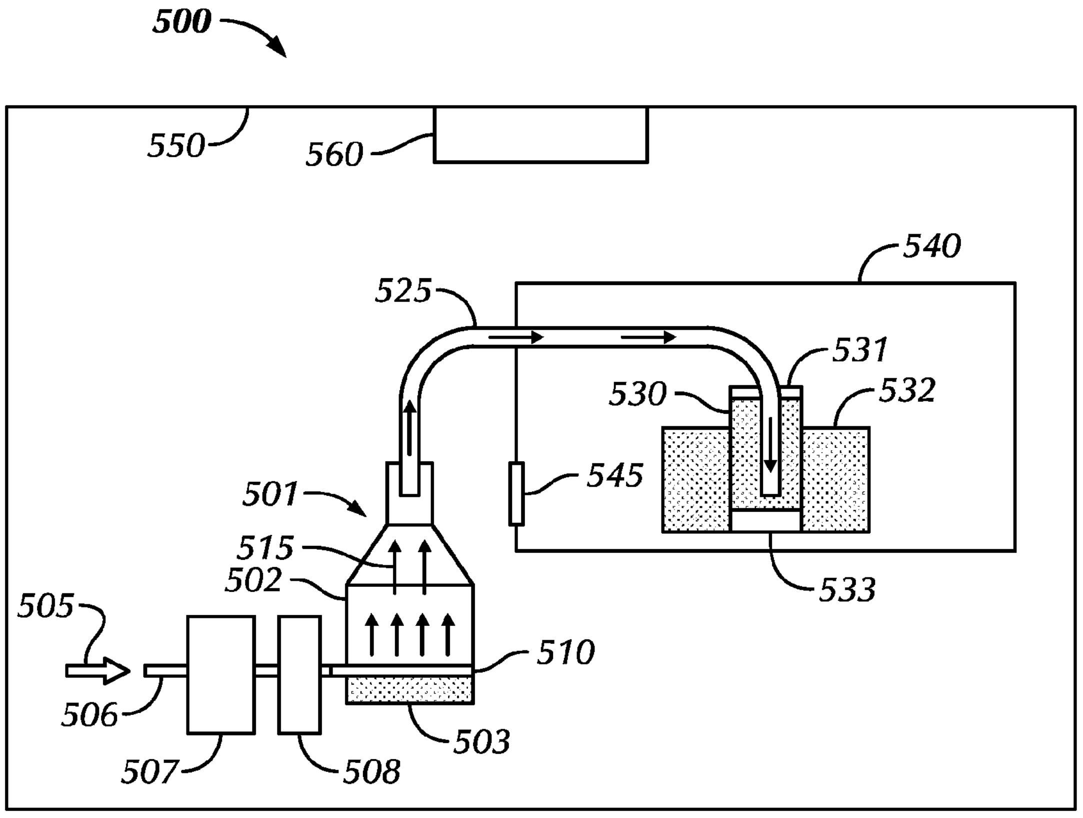
FIG. 5 is a schematic diagram of an exemplary setup for atomization of bacteriophage-containing solutions.

Referring to FIG. 5, a setup (500) can be understood as follows. The atomizing device (501) is placed within a chemical fume hood (550) with a vent (560). A prepared bacteriophage solution (503) with a known concentration of active bacterium-infective phage particles is placed into an atomization chamber (502). A source of compressed air (505) is provided to a tube (510) in an atomization chamber (502) through tubing (506). The compressed air feed may optionally be controlled by a regulator (507), and may optionally include a pressure gauge (508) downstream of the regulator. The compressed air produces an aerosol of droplets suspended in air (515) as described above. That suspension was transported via a hose (525) into a collecting chamber (540) with a HEPA filter (545). Inside the collecting chamber the aerosol flow was directed into a chilled droplet trap including an aluminum cylindrical vessel (530) with a filter (531), the vessel being at least partially surrounded by a melting water ice bath (532). The aerosol passing through the chilled droplet trap was cooled down and thus its entropy was reduced, promoting the decrease of aerosol surface area and coalescence of droplets to form bigger ones. Heavier droplets sedimented on the walls of the droplet trap and merged driven by gravity to form a liquid volume (533) on the bottom of the trap. Different air pressures may be utilized, based on the graphs seen in FIGS. 4A and 4B. At the end of each experiment the liquid accumulated in the droplet trap was transferred into a glass vial for further storage and analysis. Typical duration of one experimental run was approximately 20 min and the accumulated liquid mass was usually between 300-1000 mg. The smaller the droplets were in the generated aerosol, the less was the liquid accumulation rate in the chilled droplet trap.

Before running the atomization, liquid samples collected from the bacteriophage-containing solution used to fill the chambers of the atomizing devices were collected in the chilled droplet trap and stored in a fridge at +4° C. and then sent back to the phage lysate providers for analysis. Microbiological analysis of the bacteriophage samples was performed and the concentration of bacterium-infecting phages was determined by means of traditional plaque assay techniques (standard methods used in microbiology). The analysis is normally conducted in Petri dishes where a confluent monolayer of host cells (*Escherichia coli* bacteria was used in our study) is infected with the bacteriophages (T4 or P1 phages in our study) at varying dilutions and covered with an agar to prevent the phage multiplication from spreading indiscriminately. A tiny viral plaque is formed when a phage infects a cell within the fixed cell monolayer. Then the phage that infected the cell will lyse and multiply by spreading the infection to neighbor cells in which the infection-to-lysis cycle is repeated. As a result, the infected cell area will create a visible plaque (an area of infection enclosed by uninfected cells, similar to holes in a cheese), which can be observed by either the naked eye or using an optical microscope. Performing the plaque assay is time-consuming and can take 2-10 days until plaques are formed, depending on the viral particle being analyzed. The plaques are normally manually counted, and in combination with the dilution factor used to prepare the plate are used to calculate the number of plaque forming units per sample unit volume (pfu/mL). Based on the assumption that each formed plaque originated from one infective phage particle, the parameter "plaque forming units per sample unit volume" represents the number concentration of biologically active infective phages within the analyzed sample.

Calculating the ratio of the values of active phage concentration found in the liquid before the atomization and collected as droplets generated by an atomizer, the bacteriophage survival rate can be quantified by introducing the coefficient of bacteriophage survival ($\varepsilon$): $\varepsilon=\alpha_{N,f}/\alpha_{N,0}$, where $\alpha_{N,0}$ is number concentration of infecting bacteriophages (titer of bacteriophages) in liquid before its atomization into droplets, and $\alpha_{N,f}$ is number concentration of infecting bacteriophages in liquid sample collected from the atomized droplets. It is worth noting that $\zeta=1-\varepsilon$ represents the coefficient of bacteriophage inactivation.

Figure 6:
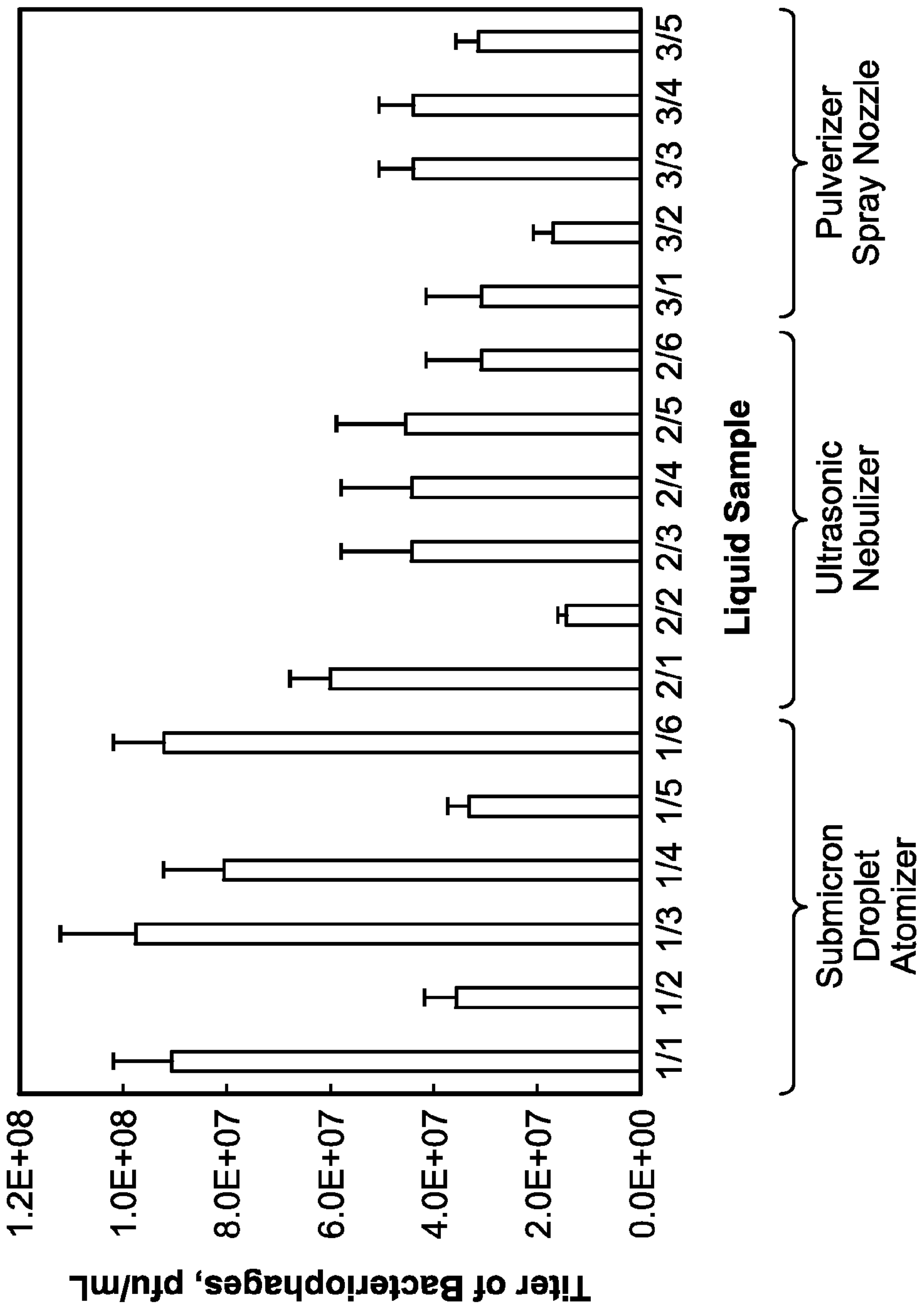
FIG. 6 is a graph showing the concentration of infecting bacteriophages T4 in liquid samples before and after atomization into droplets measured by plaque assays for different liquid atomization systems. The abscissa indicates codes of the examined liquid samples, as detailed in FIG. 7, and the ordinate shows the bacteriophage titer values in plague forming units per milliliter of phage solution.

FIGS. 6 and 7 demonstrate the experimental results of T4 bacteriophage survival rate obtained for some of the different liquid atomization systems. Comparing the coefficients of bacteriophage survival, it is found that the minimum survival rate of the T4 phages is 0.24 for various liquid atomization devices used. For the disclosed submicron droplet atomizer with mean droplet diameter of 0.2 the average coefficient of bacteriophage survival is 0.40, which is almost twice as large as the smallest observed value of 0.24 found for commercial ultrasonic nebulizer, which produced approximately 10 times bigger droplets of 3-5 μm in mean diameter (note that the non-realistic survival coefficient of 1.03 reported for the repeated experiment with the ultrasonic nebulizer was discarded as a non-reliable value). The largest average value of the coefficient of bacteriophage survival of 0.62 was observed for the pulverizer spray nozzle, which also produces the biggest droplets with 200-6001 μm in mean diameter.

The observed results for survival rate of bacteriophage T4 can be explained by various degree of mechanical and chemical stresses applied on the phage-containing liquid by different atomization systems. Ultrasonic waves are known to induce micro-cavitation phenomena affecting biological liquids, thus ultrasonic nebulization can be harmful for bacteriophages resulting in their low survival rates. The manually driven pulverizer spray nozzle applies relatively low mechanical stress, disintegrating liquid into submillimeter-size droplets. Correspondingly, the bacteriophage survival rate of the pulverizer spray nozzle is relatively high, though even it indicates inactivation of around 40% of the initially infecting phages. Finally, the disclosed system of liquid atomization into submicron-size droplets of 0.2 μm in mean diameter (as noted above, it is much smaller than achieved by conventional atomization methods), demonstrates promising survival rate of bacteriophages lying in between the ultrasonic nebulizer and the pulverizer spray nozzle. Provided the evaporation time of solvent is proportional to the square of a droplet diameter, the expected droplet-to-particle conversion time for an aerosol production system of bacteriophage-containing particulate materials will be 100-100,000 times shorter for the disclosed submicron droplet atomizer than that for conventional liquid atomization systems.

Owing to very fine atomized droplets, the disclosed submicron droplet atomizer enables the utilization of room-temperature air for aerosol drying-induced particle formation, in contrast to conventional systems using temperatures either much higher (>45° C. for spray drying/agglomeration/coating) or much smaller (spray freeze drying when droplets are subjected to saturated liquid nitrogen at −196° C.) than normal room temperature. Given this and the observed coefficient of phage survival, the disclosed system for aerosol production of bacteriophage-containing particles equipped with submicron droplet atomizer is expected to have much higher overall bacteriophage survival rate than in existing systems like spray drying and spray freeze drying that apply large mechano-chemical stresses and lead to low 1:1000-1:1,000,000 phage survival rates.

Example 2

Using the graphs of FIGS. 4A and 4B, stable solutions of HOCl-water and hydrogen peroxide have been converted into submicron aerosol droplets. With $\Delta p_{gj}$ of, e.g., 1-5 bar, particle sizes between 100 nm and 1 μm could be achieved. At higher pressures, the particle size could be reduced, and at lower pressures, the particle size could be increased.

Example 3

Using the graphs of FIGS. 4A and 4B, solutions of budesonide dispersed in water are expected to be able to be converted into submicron aerosol droplets. With $\Delta p_{gj}$ of, e.g., 1-5 bar, particle sizes between ~100 nm and 1 μm could be achieved. At higher pressures, the particle size could be reduced, and at lower pressures, the particle size could be increased.

Example 4

Using the graphs of FIGS. 4A and 4B, solutions of a hemp oil emulsion are expected to be able to be converted into submicron aerosol droplets. With $\Delta p_{gj}$ of, e.g., 1-5 bar, particle sizes between ~100 nm and 1 μm could be achieved. At higher pressures, the particle size could be reduced, and at lower pressures, the particle size could be increased. Using identical configurations, two different commercially available hemp oil solutions (one at a concentration of 33 mg/mL, and one at a concentration of 100 mg/mL), both with viscosities in the range of 30-60 mPa-s, were converted into submicron aerosol droplets. As these solutions were sold as nutritional supplements, the hemp oil solutions contained additional components beyond hemp oil extract, such as omega 3, omega 6, omega 9, and vitamins C and E.

Example 5

Various concentrations (e.g., 0.5-15% wt.) of solutions of sodium chloride in deionized water was prepared by mixing the crystals of table salt (NaCl) with deionized water at 45° C. for 15 min. The procedure for preparing precursor of silica ($SiO_2$) was: tetraethoxysilane (TEOS), ethanol, deionized water, and HCl (mole ratio 1:3.8:1:5×10−5) were mixed at 60° C. for 120 min and then aged at room temperature under continuous stirring up to 43 hours. For synthesis of titania ($TiO_2$) particles, titanium (IV) tetraisopropoxide (TIPT) and titanium (IV) butoxide (TBT)-based precursors were utilized. The TIPT-based precursor of $TiO_2$ was prepared in 3 steps: a) TIPT was slowly added into acetylacetone (acac) and mixed for 15 min; b) acetic acid was added dropwise in deionized water and stirred; c) TIPT-acac solution was added dropwise into aqueous acetic acid solution, and then stirred for 20 min under 45° C., yielding a yellow transparent solution with final reactant mole ratio TIPT:acac:acetic acid:water=1:1:1:136. A TBT-based sol was made in similar steps to TIPT-based precursor, however ethanol was used instead of water; the final mole ratio of the reactants was TIPT:acac:acetic acid:ethanol 1:1:0.2:6.9.

NaCl-water solutions of different concentrations, a $SiO_2$ sol and two types of $TiO_2$ sols—titanium (IV) tetraisopropoxide and titanium (IV) butoxide—were prepared as described. The $SiO_2$ sol was aged up to 43 hours. First, the precursor liquids were atomized using compressed air supplied under 1.5 bar gauge pressure (for NaCl-water solutions, silica and TBT-based sols) and 2.5 bar gauge pressure (for TIPT-based sol), and the synthesized nanoparticles were collected and studied using scanning electron microscopy. The higher atomizing pressure for TIPT-based sol was applied due to considerably lower droplet flow rates, compared to the other precursors, obtained at the air pressure of 1.5 bar gauge. In additional experiments, the atomizing air pressure was varied in the range 1-3 bar gauge.

For the salt solutions, the temperature and relative humidity of room air used for drying of droplets were ~23° C. and ~30% respectively. Analysis of the morphology of the NaCl particles demonstrates two main groups present in the same sample: (a) dimpled cube-shaped particles typically 300-500 nm in size and (b) spheroidal particles with sizes smaller than 300 nm. In a typical sample, the number of sphere-like NaCl particles was found to be larger than the number of cubic particles, and the mean particle size was 227 nm. The observed non-cubic morphology may be attributed to their amorphous structure obtained due to rapid water evaporation from the initial submicron droplets of the salt solution, when the time of crystal lattice formation was greater than the drying time of the droplet. Using a previously developed model, evaluation of the drying time of a 200 nm diameter droplet of 5% wt. NaCl-water solution under laboratory air conditions is about of 40 μs and yields a final average particle diameter of ≈55 nm. More generally, for 5% wt. NaCl-water droplets of initial diameter 20-2000 nm covering size distribution of the produced aerosol, the estimated characteristic drying time spans between 0.4-4000 μs, while the droplets shrink approximately 3.5 times before turning into dry particles. Provided the measured air velocity used to dry the droplets is ~0.1-0.5 m/s (laminar flow, Re=300-1600), in terms of the drying kinetics of a single droplet, the generated droplets are expected to turn into dry particles after traveling 0.04-400 μm in room air, whereas the overall particle residence time in the setup is ~1-5 s, which is much longer than the needed drying time.

$SiO_2$ xerogel particles were synthesized for silica sol aging times of 23, 27.5 and 32 hours. In these experiments, the gauge pressure of compressed air used for precursor atomization was 1.5 bar, and the temperature and relative humidity of room air used for drying of droplets were similar to previous experiments with NaCl, ~23° C. and ~30% respectively. For the same operating conditions and sol aging times of 2.5, 9 and 43 hours, not separate particles but continuous silica films with cracked or irregular surface morphologies were obtained. These observations can be explained by different stages in the progress of the chemical reaction in the utilized silica sol, which changes the sol properties in time, and thus has a direct effect on the droplet drying kinetics and the ability of the sol droplets to form particles once the solvent evaporates. Particles of spherical morphology were obtained. The smallest $SiO_2$ xerogel particles had mean diameter of 417 nm and were obtained for the sol aged 27.5 hours, and this size is about 1.8 times bigger than that of the NaCl particles.

The titania xerogel demonstrate formation of both particles and continuous thin films, depending on the composition of the titania sol and are independent of the sol aging time. The visible cracks in the thin film appeared during SEM characterization in high-vacuum mode. The gauge pressure of the compressed air used for atomization of TBT-based precursor was 1.5 bar, whereas for TIPT-based precursor a higher gauge pressure of 2.5 bar was applied due to considerably lower rate of the droplet generation at 1.5 bar. The temperature and relative humidity of room air used for drying of droplets were ~23° C. and ~30% respectively, the same as for the experiments with NaCl and $SiO_2$ particles synthesis. The analysis reveals smooth spherical morphology of the final product and that the mean size of the obtained particles is 106 nm from the TIPT-based sol, which is the smallest mean particle size measured in this example.

It should be noted that the NaCl atomization discussed above can be analogized to the atomization of most commercially available pharmaceutical ingredients. In at least some instances, APIs may be provided as solutions (either aqueous or oil-based), which contain the active material (i.e., a small molecule) in a solvent. The small molecules are much smaller than the droplet sizes produced here. As such, it is expected that any API can be atomized into submicron droplets using a similar approach to the example provided here.

Example 6

Gasoline, petroleum diesel fuel, and 0.1-2% wt. aqueous solutions of sodium alginate were used to produce aerosol droplets. Air and carbon dioxide gas were supplied at pressures between 0.5 and 4 bar gauge. All three produced droplets having number mean particle sizes of roughly between 100 and 200 nm.

Those skilled in the art will recognize, or be able to ascertain using no more than routine experimentation, many equivalents to the specific embodiments of the invention described herein. Such equivalents are intended to be encompassed by the following claims.

What is claimed:

1. A method for creating aerosols of droplets, aerosols of particles, or powders, comprising:

providing a liquid comprising a dispersed viable biological material selected from one or more of a virus, a cell, a tissue, or an organism;

aerating the liquid in an atomization chamber to form bubbles, such that the bubbles rise to a surface of the liquid;

forming a submicron droplet aerosol having the dispersed viable biological material in a plurality of droplets by causing a gas jet to be directed through an opening in a tube towards at least one of the bubbles in the atomization chamber and controlling a ratio of energy rates supplied by the gas jet and dissipated by liquid surface tension of the at least one of the bubbles, thereby resulting in the plurality of droplets of the submicron droplet aerosol having a diameter of 0.2-1 μm;

optionally forming a dry particle aerosol via solvent evaporation of the submicron droplet aerosol; and optionally forming a powder of submicron or nanostructured particles by passing the dry particle aerosol through a particle collector.

2. The method according to claim 1, wherein a pressure of a gas provided to the tube in order to cause the gas jets is based on a viscosity of the liquid.

3. The method according to claim 1, wherein a viscosity of the liquid is between 5 and 1000 times the viscosity of water.

4. The method according to claim 1, wherein the solvent evaporation involves subjecting the droplet aerosol a gas having a temperature between 0° C. and 120° C.

5. The method according to claim 1, wherein the solvent evaporation includes lyophilization.

6. The method according to claim 1, wherein the submicron droplet aerosol or dry particle aerosol is then provided to a patient.

7. The method according to claim 6, wherein the patient is being treated with a ventilation machine, and the submicron droplet aerosol or dry particle aerosol is introduced in-line with the ventilation machine.

8. The method according to claim 1, wherein the dispersed viable biological material comprises a virus, wherein the virus comprises a bacteriophage.

* * * * *